(12) United States Patent
Northrup, III et al.

(10) Patent No.: US 6,916,327 B2
(45) Date of Patent: Jul. 12, 2005

(54) DEVICE FOR CREATING AN ANASTOMOSIS, INCLUDING PENETRATION STRUCTURE AND EVERSION STRUCTURE

(75) Inventors: William F. Northrup, III, Edina, MN (US); Joanne B. Northrup, Edina, MN (US)

(73) Assignee: Metacardia, Inc., Edina, MN (US)

( * ) Notice: Subject to any disclaimer, the term of this patent is extended or adjusted under 35 U.S.C. 154(b) by 485 days.

(21) Appl. No.: 09/800,613

(22) Filed: Mar. 7, 2001

(65) Prior Publication Data

US 2001/0037120 A1 Nov. 1, 2001

Related U.S. Application Data

(60) Provisional application No. 60/187,428, filed on Mar. 7, 2000, and provisional application No. 60/201,594, filed on May 3, 2000.

(51) Int. Cl.[7] .............................. A61B 17/08; A61D 1/00
(52) U.S. Cl. ...................... 606/153; 606/157; 606/219; 606/220; 606/221
(58) Field of Search ................................. 606/153, 155, 606/156, 157, 158, 219, 220, 221, 216, 217, 232, 233

(56) References Cited

U.S. PATENT DOCUMENTS

| | | | |
|---|---|---|---|
| 233,475 A | 10/1880 | Cook et al. | |
| 2,254,620 A | * 9/1941 | Miller | ......................... 606/221 |
| 2,910,067 A | * 10/1959 | White | ......................... 606/221 |
| 3,068,870 A | * 12/1962 | Brown | ......................... 606/221 |
| 3,273,562 A | * 9/1966 | Levin | ......................... 606/221 |
| 3,316,914 A | 5/1967 | Collito | |
| 3,378,010 A | * 4/1968 | Codling et al. | ............. 606/157 |
| 3,606,888 A | 9/1971 | Wilkinson | |
| 3,845,772 A | 11/1974 | Smith | |
| 3,857,396 A | 12/1974 | Hardwick | |
| 4,006,747 A | * 2/1977 | Kronenthal et al. | ........ 606/144 |
| 4,625,727 A | 12/1986 | Leiboff | |
| 4,732,151 A | 3/1988 | Jones | |
| 4,899,744 A | 2/1990 | Fujitsuka et al. | |
| 4,901,721 A | 2/1990 | Hakki | |
| 4,983,176 A | * 1/1991 | Cushman et al. | ........... 606/151 |
| 5,002,563 A | 3/1991 | Pyka et al. | |
| 5,009,663 A | 4/1991 | Broome | |
| 5,041,129 A | 8/1991 | Hayhurst et al. | |
| 5,074,874 A | 12/1991 | Yoon et al. | |
| 5,123,913 A | 6/1992 | Wilk et al. | |

(Continued)

FOREIGN PATENT DOCUMENTS

| | | |
|---|---|---|
| WO | 98/30152 | 7/1998 |
| WO | 98/30153 | 7/1998 |
| WO | 99/21490 | 5/1999 |
| WO | 99/62406 | 12/1999 |
| WO | 99/62409 | 12/1999 |

*Primary Examiner*—Henry Bennett
*Assistant Examiner*—Kathryn Odland
(74) *Attorney, Agent, or Firm*—Dicke, Billig & Czaja, PLLC (57) ABSTRACT

A surgical staple for use in creating an everted anastomosis of at least two anatomical structures includes a bendable staple body. At least two evening elements protrude from the staple body. Spacing elements and a penetrating element also are provided. In use, the evening elements and spacing elements are apposed, and inner layers of the anatomical structures are held together to form an evened anastomosis. The evening platforms are disposed on an outer radius of the closed staple, and the penetrating element is disposed on a different, inner radius, to ensure that the penetrating element is excluded from the lumen of the anastomosis. Embodiments of the invention substantially ensure intima-to-intima approximation completely circumferentially at the anastomotic site, with no portion of cut tissue edges, suture or staple exposed to the lumen of the anastomosis. Cut tissue edges, as well as the staple, are completely extra-lumenal. Related methods provide similar advantages.

30 Claims, 8 Drawing Sheets

U.S. PATENT DOCUMENTS

| | | | |
|---|---|---|---|
| 5,171,252 A | * 12/1992 | Friedland | 606/151 |
| 5,263,973 A | * 11/1993 | Cook | 606/216 |
| 5,269,809 A | 12/1993 | Hayhurst et al. | |
| 5,500,000 A | 3/1996 | Feagin et al. | |
| 5,527,341 A | 6/1996 | Gogolewski et al. | |
| 5,665,109 A | 9/1997 | Yoon | |
| 5,810,851 A | 9/1998 | Yoon | |
| 5,810,853 A | 9/1998 | Yoon | |
| 5,879,371 A | 3/1999 | Gardiner et al. | |
| 5,957,938 A | * 9/1999 | Zhu et al. | 606/149 |
| 5,972,024 A | 10/1999 | Northrup et al. | |
| 5,976,159 A | 11/1999 | Bolduc et al. | |
| 5,993,468 A | * 11/1999 | Rygaard | 606/151 |
| 6,120,525 A | 9/2000 | Westcott | |
| 2001/0051816 A1 | 12/2001 | Enzerink et al. | |

* cited by examiner

DEVICE FOR CREATING AN ANASTOMOSIS, INCLUDING PENETRATION STRUCTURE AND EVERSION STRUCTURE

CROSS-REFERENCE TO RELATED APPLICATIONS

The subject matter of this application is related to the subject matter of commonly assigned U.S. applications Ser. Nos. 60/187,428, filed Mar. 7, 2000 and 60/201,594, filed May 3, 2000, both of which are incorporated herein by reference and priority to which is claimed under 35 U.S.C. §119(e).

BACKGROUND OF THE INVENTION

1. Field of Invention

The invention relates to devices and methods for anastomosing two or more anatomical structures, such as vascular structures. Embodiments according to the invention are desirable in both minimally invasive and conventional surgical situations. Certain embodiments have particular application to minimally invasive direct coronary artery bypass (MIDCAB) and off-pump (OPCAB) procedures, for example.

2. Description of Related Art

Surgical connections (anastomoses) between two tubular structures of soft tissue (e.g. blood vessels) typically are fashioned with "linkage" devices, such as flexible suture or rigid staples. Such anastomoses involve surgical incisions of the two soft tissue structures, which result in cut edges. These edges ideally are excluded from the inside channel (lumen) of the two joined structures. Ideally, the linkage devices are also excluded from the lumen.

The suture- and staple-type linkage devices of the prior art, however, do not always achieve the above-described ideal; cut tissue edges and the linkage devices themselves sometimes are exposed to the lumen. See FIGS. 1A–1D, for example, which show unpredictable eversion and exclusion of cut edges 10 (of ends 20, 30 of anatomical structures 40, 50) and suture 60 from lumen 70 when sutures alone are used, as in the prior art.

SUMMARY OF THE INVENTION

In view of these and other disadvantages, a need exists for devices and methods that consistently, predictably and reliably evert the edges of an e.g. circumferential anastomosis between two tubular anatomical structures, e.g. a vascular anastomosis between the left internal mammary artery and the left anterior descending coronary artery. Such devices and methods can be used alone, or in conjunction with a biological adhesive product, suture, or other supplemental products or devices. They can be part of a sutured or stapled anastomosis, i.e. an anastomosis using one or more sutures and/or staples in combination with the devices of the invention.

The ultimate purpose, according to embodiments of the invention, is to substantially ensure inner-layer-to-inner-layer (e.g. intima-to-intima) approximation completely circumferentially at the anastomotic site, with no portion of the cut edges of the tissues or suture or staple exposed to the lumen of the anastomosis. Instead, embodiments of the invention substantially ensure that the cut edges of the tissues, as well as the linkage device, are completely extraluminal. With such embodiments, the entire circumference of both structures of the anastomosis is completely everted.

Embodiments of the invention provide a number of advantages. For example, the invention provides a more precise, completely everted anastomosis more predictably than heretofore possible with staples or suture alone. Embodiments of the invention are believed to result in a higher patency rate in vascular anastomoses, by eliminating cut edges of tissue or foreign bodies (e.g. sutures or staples) from the lumen. Such tissue edges or foreign bodies, if left exposed to the lumen, can threaten the patency of the anastomosis by allowing thrombus (clot) formation and/or fibrosis or intimal hyperplasia (scarring), ultimately resulting in stenosis (narrowing) or occlusion. Embodiments of the invention, on the other hand, cause immediate and long-term improvements in patency and therefore quality of life and longevity.

Further, embodiments of the invention allow a smaller number of anastomotic eversion devices to be used, e.g. in conjunction with a biological adhesive or equivalent. Such hybrid procedures allow for a simpler, more expeditious anastomosis, with either conventional or minimally invasive techniques, with or without the aid of cardiopulmonary bypass.

Still further, according to embodiments of the invention, everting platforms on an outer radius of a closed everting staple assure that a penetrating element of the staple is excluded from the lumen, because the penetrating element is on a different, inner radius. Spacing elements according to the invention assure a space between everting platforms of the staple in a closed configuration of the staple, negating any tissue necrosis at the level of intima-to-intima approximation.

Penetrating and spacing elements according to embodiments of the invention may cause tissue damage, but such damage is outside of the anastomosis, i.e. it is at or near the inner radius of the closed staple. Nevertheless, spacing elements and/or penetrating elements according to such embodiments have small surface area, to minimize tissue necrosis. To effect parallel alignment of the everting platforms, the staple is "scissored" in the closed position thereof. One of the everting platforms is offset accordingly.

By providing two everting platforms on a single piece of wire or other material constituting the staple, according to embodiments of the invention, the need to deliver an opposing everting platform from an opposite side of an anastomosis is eliminated. Other features and advantages according to embodiments of the invention will become apparent from the remainder of this application.

BRIEF DESCRIPTION OF THE DRAWINGS

Embodiments of the invention will be described with reference to the figures, in which like reference numerals refer to like elements and in which:

FIG. 3 shows an outer radius of the illustrated everting platforms, an inner radius of the spacing and penetrating elements, and side-by-side offset axes of the closed staple;

DETAILED DESCRIPTION OF PREFERRED EMBODIMENTS

A first embodiment of surgical staple 100 for creating a completely everted anastomosis is shown in FIGS. 2–9. Staple body 110 of surgical staple 100 is constructed to bend, e.g. at 120 in FIG. 3. At opposite ends of staple body 110, staple 100 includes everting platforms or elements 130, 140 that protrude from staple body 110. Everting platform 130 is centered with respect to longitudinal axis 145 of staple body 110. As illustrated, a central portion 146 of everting platform 130 is connected to the very end of staple body 110. Everting platform 140, on the other hand, is connected to staple body 110 at its end 148, not at a central portion thereof. Thus, as shown in e.g. FIGS. 8–9, everting platforms 130, 140 are offset with respect to each other, in a transverse direction with respect to axis 145.

Surgical staple 100 also includes first spacing element 150, disposed adjacent staple body 110 at the very end thereof. Specifically, spacing element 150 is adjacent to longitudinal axis 145 thereof and above everting platform 130, as viewed in e.g. FIGS. 2 and 8. Staple 100 also includes second spacing element 160, disposed along staple body 110 at the opposite end thereof and generally in line with longitudinal axis 145 thereof. Spacing elements 150, 160 are closer to the middle of staple body 100 than are everting platforms 130, 140. Spacing elements 150, 160 can be generally tapered, as shown at e.g. 165 in FIGS. 2 and 8. Of course, other placements and shapes of spacing elements 150, 160 are contemplated.

Penetrating element 170 is constructed to penetrate the anatomical structures being anastomosed, in a manner to be described, and is disposed at one end of staple body 110. Penetrating element 170 is disposed generally along longitudinal axis 145 of staple body 110 and is generally perpendicular or transverse, or otherwise angled, to it.

Figure 1A:
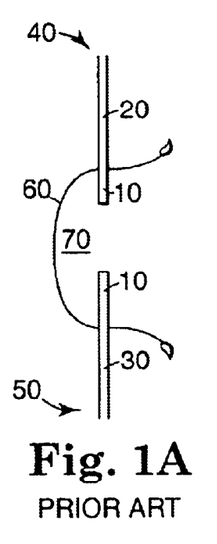
FIGS. 1A–1D show one type of prior art anastomosis technique using a suture alone, with unpredictable eversion and exclusion of cut edges and suture from the lumen.
Figure 1B:
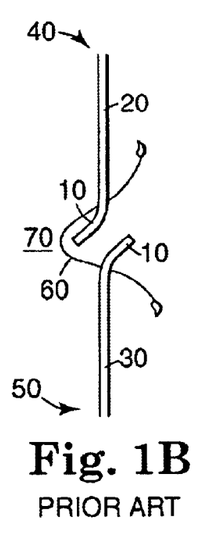
Figure 1C:
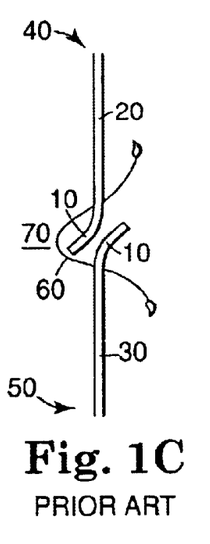
Figure 1D:
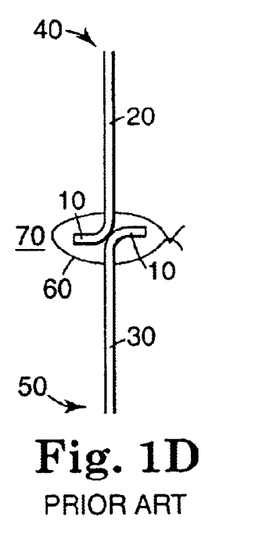
Figure 2:
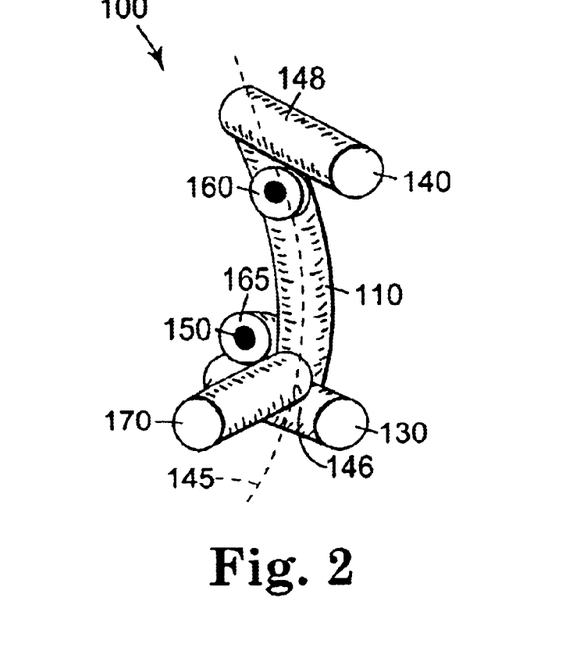
FIG. 2 is a panoramic view of an open staple according to an embodiment of the invention, with an everting platform, offset everting platform, two spacing elements and penetrating element as shown.
Figure 3:
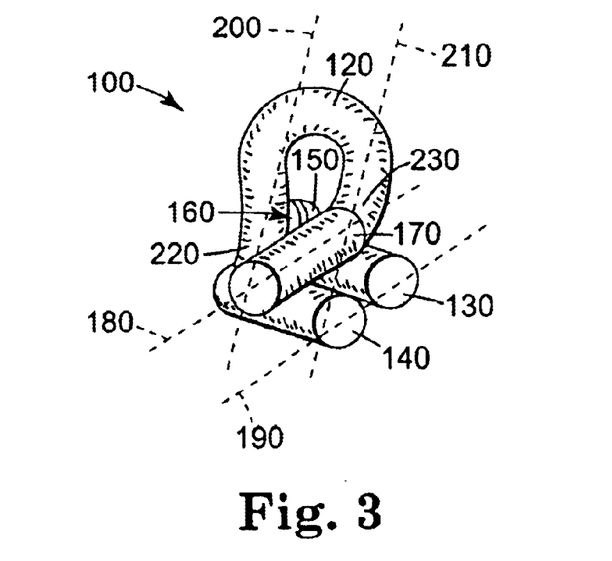
FIG. 3 is a panoramic view of a closed, "scissored" staple with two radii and two axes according to an embodiment of the invention. More specifically.
Figure 4:
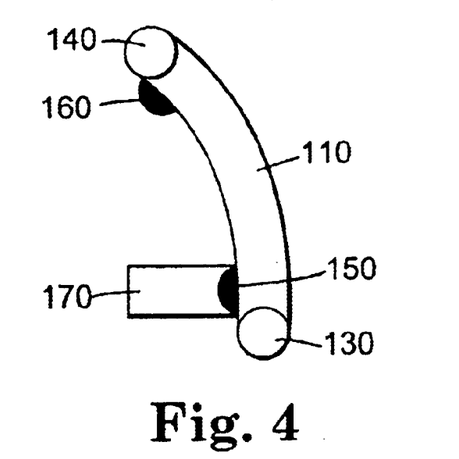
FIG. 4 is a side view of a staple according to an embodiment of the invention, showing the penetrating element, spacing elements, and everting platforms.

Staple 100 is constructed to bend from the straight or non-use or open configuration illustrated in FIGS. 2 and/or 4 to the bent or "scissored" or closed configuration of FIG. 3. In the FIG. 3 configuration, everting platforms 130, 140 are disposed generally parallel to each other on the same side of penetrating element 170, e.g. the underside as viewed in FIG. 3. Additionally, everting platforms 130, 140 are apposed, as are spacing elements 150, 160.

As illustrated in FIG. 3, spacing elements 150, 160 and penetrating element 170 generally define elevation line 180. Everting platforms 130, 140 generally define elevation line 190. Lines 180, 190 define distances from bend 120 that can be considered inner and outer radii, respectively. Because line 180 is closer to bend 120, line 180 can be considered to define an inner radius of staple 100. Similarly, line 190 can be considered to define an outer radius of staple 100. Additionally, FIG. 3 illustrates side-by-side offset axes 200, 210 of staple 100. Axes 200, 210 are offset from each other in two dimensions, e.g. a first dimension as viewed in the direction of lines 180, 190, and a second dimension as viewed in the direction of everting platforms 130, 140, in FIG. 3. In its closed configuration, staple 100 is bent in a "U" shape to form two legs 220, 230 separated by bend 120. Legs 220, 230 are disposed along axes 200, 210 and thus are offset from each other in two dimensions.

Figure 5:
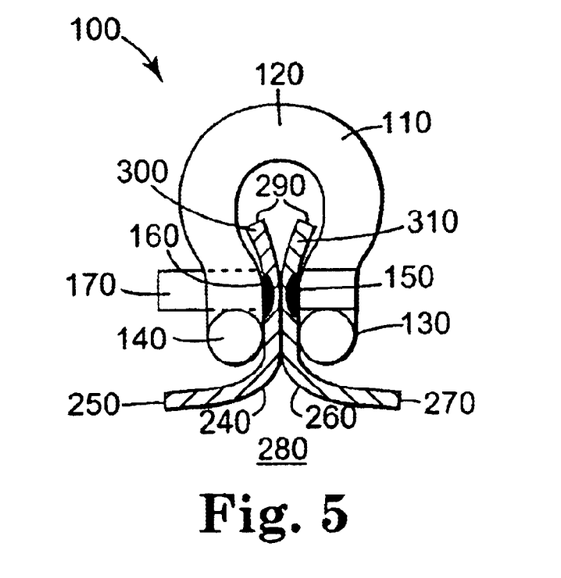
FIG. 5 is a side view of closed staple enclosing tissue, according to an embodiment of the invention, showing the penetrating element, everting platforms and spacing elements.
Figure 6:
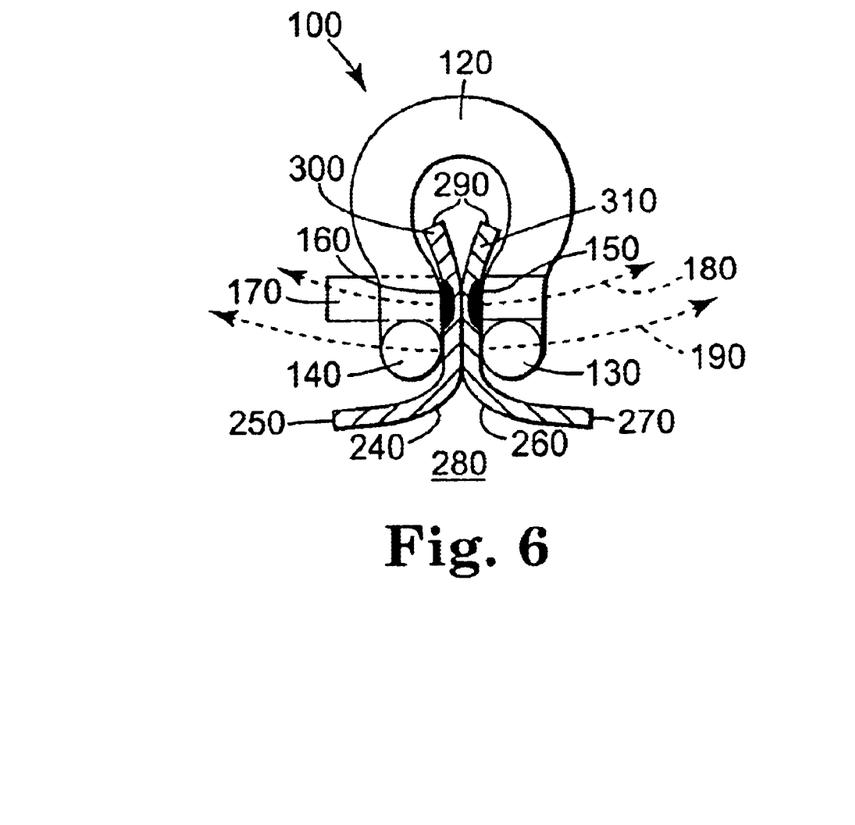
FIG. 6 is a side view showing the inner radius of the spacing and penetrating elements and the outer radius of the everting platforms.
Figure 7:
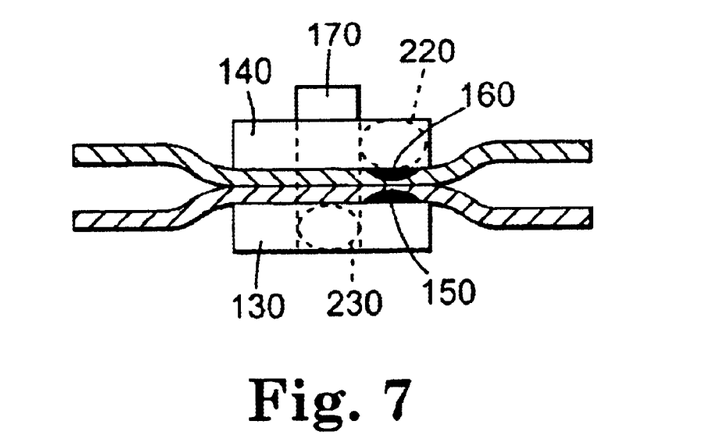
FIG. 7 is an end view of a closed staple enclosing tissue, according to an embodiment of the invention, showing the penetrating element, everting platforms and spacing elements.

FIGS. 5–7 show staple 100 in use. As shown, staple 100 joins inner layer (intima) 240 of anatomical structure 250 to inner layer (intima) 260 of anatomical structure 270. Staple 100 keeps lumen 280 between anatomical structures 250, 270 free of exposure to cut tissue edges 290, ends 300, 310 of anatomical structures 250, 270, and all portions of staple 100 itself, including penetrating element 170. Lumen 280 is also free of suture and other foreign bodies. Thus, staple 100 causes immediate and long-term improvements in the patency of the anastomosis by reducing the likelihood of clot formation, scarring, stenosis and other complications.

When staple 100 is in its closed configuration around cut ends 300, 310 of anatomical structures 250, 270, spacing elements 150, 160 are in an apposed relationship and cut ends 300, 310 are held together between spacing elements 150, 160. Additionally, everting platforms 130, 140 are in an apposed relationship, with cut ends 300, 310 held together between everting platforms 130, 140. Penetrating element 170 penetrates ends 300, 310. The distance between apposed spacing elements 150, 160 is less than the distance between apposed everting platforms 130, 140, as shown. As shown in e.g. FIG. 6, apposed spacing elements 150, 160 and/or penetrating element 170 define inner radius 180 of closed staple 100, and apposed everting platforms 130, 140 define outer radius 190 of closed staple 100, radii 180, 190 being considered to originate at bend 120 in staple 100. Because penetrating element 170 is on the different, inner radius 180, it is generally assured that penetrating element 170 is excluded from lumen 280.

Figure 8:
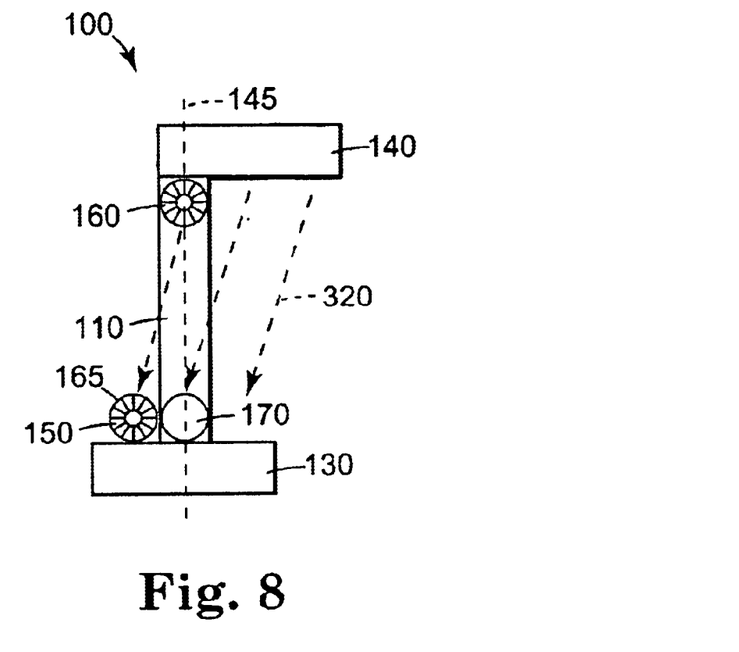
FIG. 8 is an inside view of a open staple, according to an embodiment of the invention, showing the penetrating element, everting platforms and spacing elements, and the direction of closure of the staple.
Figure 9:
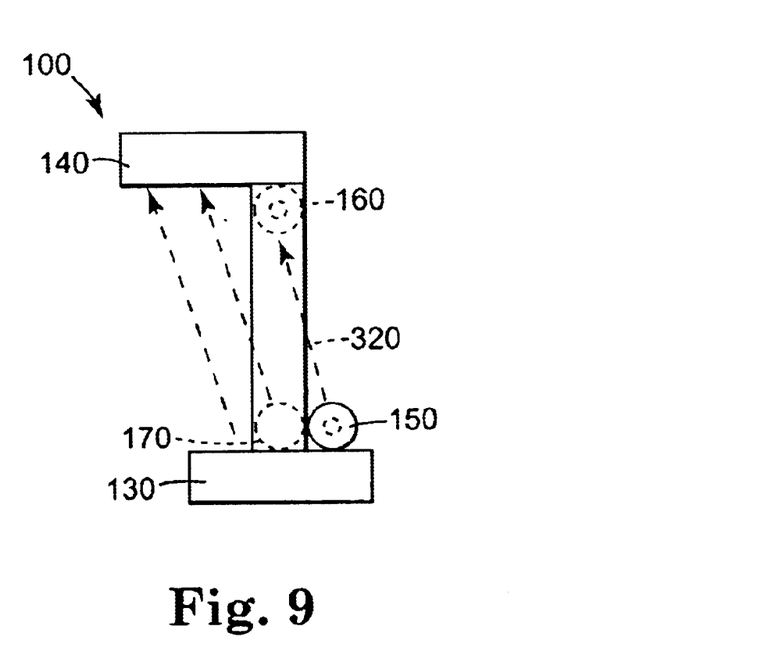
FIG. 9 is an outside view of an open staple, according to an embodiment of the invention, showing the penetrating element, everting platforms and spacing elements, and the direction of closure of the staple.

As shown in FIGS. 8–9, everting platform 140 moves laterally or transversely with respect to staple body 110 as staple 100 is closed, such that the direction of closure 320 is at an angle to staple body 110. A method of bending a surgical staple according to an embodiment of the invention includes moving everting platform 140, disposed at one end of staple 100, to be parallel to and adjacent to everting platform 130 disposed at an opposite end of staple 100.

Spacing element 160 disposed at one end of staple 100 becomes apposed to spacing element 150 disposed at the opposite end of staple 100. Spacing elements 150, 160 are disposed adjacent to and generally parallel to penetrating element 170. Everting platform 140 moves in direction of closure 320 to its disposition parallel to and adjacent to everting platform 130. Direction of closure 320 is disposed at an angle, e.g. about 15° to about 20°, to longitudinal axis 145 extending between everting platforms 130, 140. Thus, everting platforms 130, 140 are moved from an offset configuration, illustrated in FIG. 8, in which platforms 130, 140 are offset from each other along their respective longitudinal axes, to a non-offset configuration, illustrated in e.g. FIG. 3, in which everting platforms 130, 140 are aligned with each other.

Turning to FIGS. 10–15, staple devices according to embodiments of the invention include two main parts. The first part is staple 400, defining a generally curved shape and supporting a fixed eversion platform 410 securely and immovably affixed thereto, according to one embodiment. Staple 400 can be a free-standing staple, or attached to a suture or other delivery system, for example. The second part is free eversion platform 420, which is supportable by staple 400 and slidable relative thereto in a "threaded" relationship.

Both staple 400 and free eversion platform 420 preferably have a substantially "D"-shaped cross section 430, to predictably orient eversion platform 420. Of course, other cross-sectional shapes of the staple and free eversion platform are contemplated, according to embodiments of the invention. Staple 400 and platform 420 preferably are made of a biocompatible material. At least the staple is malleable, according to a preferred embodiment, so that it can be crimped into a closed position with a closing or crimping device. According to other embodiments, described below, a memory metal eliminates or reduces the need for a separate closing device.

Free eversion platform 430 generally comprises two parts: collar or spacing element 440 and eversion body or platform 450. Eversion platform 450 preferably is made of a biocompatible material similar to staple 400. However, it is substantially non-deformable, according to this embodiment. Collar 440 slightly overhangs eversion platform 420 in the axis of staple 460, as indicated at 460 in FIG. 11. Overhang 460 substantially prevents apposing eversion platforms 410, 420 from crushing cut ends 470, 480 of vascular or other structures 490, 500 in the anastomosis, by keeping them slightly separated from one another in the closed position. Thus, any tissue in the anastomosis is approximated without being strangulated. Additionally, lumen 510 is kept free of exposure to cut tissue edges 520, 530, staple 400, eversion platforms 410, 420, suture, or other structures that might threaten the patency of the anastomosis.

Figure 10:
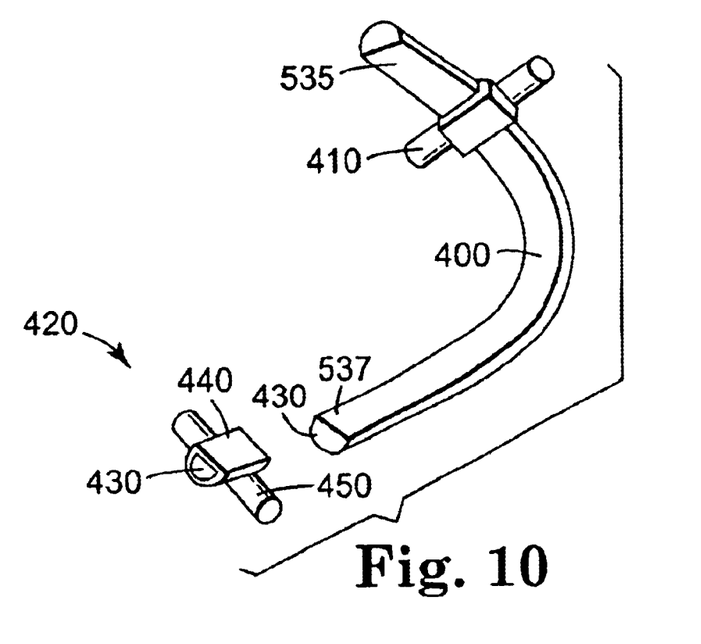
FIG. 10 is a perspective view of a staple and an eversion platform, according to an embodiment of the invention.
Figure 11:
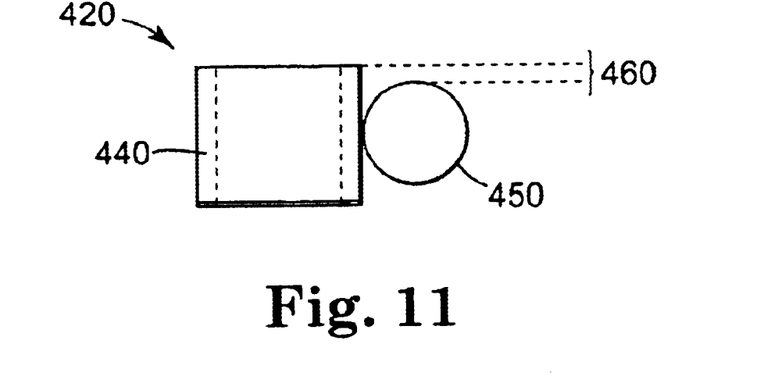
FIG. 11 is a side view of an eversion platform with overhanging collar, according to an embodiment of the invention.
Figure 12:
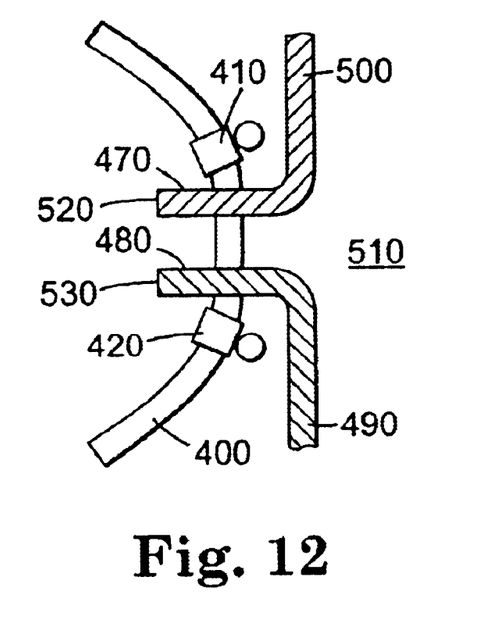
FIG. 12 is a side, cross-sectional view of a stapled anastomosis in a staple-open, platforms-apart configuration.
Figure 13:
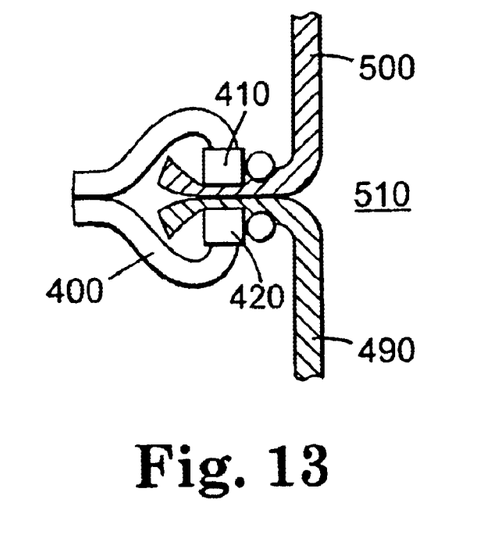
FIG. 13 is a side, cross-sectional view of a stapled anastomosis in a staple-closed, platforms-apposed configuration.

According to embodiments of the invention, either eversion platform 410, 420 illustrated in e.g. FIG. 10 can be fixed or free, or both can be free. Everting staple 400 likely is easier to deploy, however, if one platform is fixed and the other is free, as illustrated. Structurally, platforms 410, 420 are generally identical according to one embodiment.

According to the illustrated embodiment, fixed eversion platform 410 is nearer trailing end 535 of staple 400, especially when it is to be deployed via a suture or other delivery mechanism. Suture can be attached to the leading end 537 of the staple, for example, and free eversion platform 420 deployed after engaging and penetrating the two vascular or other structures 490, 500 with staple 400.

The body of staple 400, or a portion thereof, thus is a penetrating element. According to one embodiment, free eversion platform 420 is threaded over a needle and suture, is advanced along the suture to staple 400, and then is advanced to a desired position along staple 400 as shown in e.g. FIG. 12. A closing/crimping device or other means then brings the paired eversion platforms 410, 420 into final juxtaposition to each other as staple 400 is closed, in the manner of e.g. FIG. 13. Eversion platforms 410, 420 are the fulcrum for closing staple 400.

Of course, two separate free eversion platforms 410 can be employed, with neither affixed to staple 400 at least until after staple 400 engages the two vascular structures 490, 500. The free eversion platforms slide over suture and/or the respective ends of staple 400, while staple 400 is still in an open position. According to this embodiment, and/or according to those described earlier, suture can be attached to either or both ends of staple 400.

Figure 14:
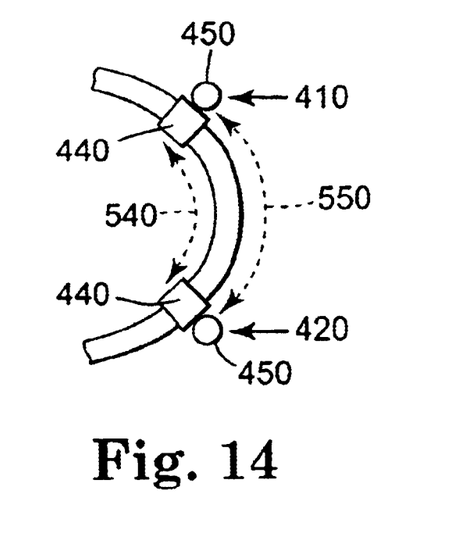
FIG. 14 is a side view showing the inner radius of the staple and the outer radius of the eversion platforms.
Figure 15:
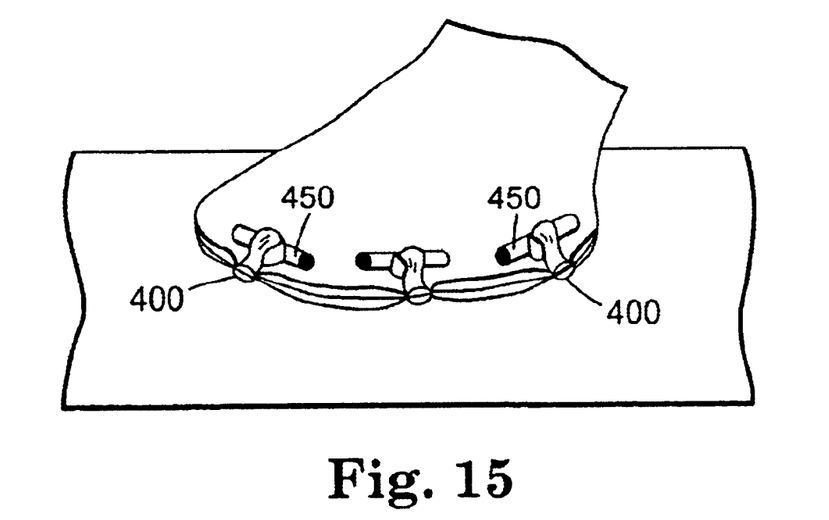
FIG. 15 is a panoramic view of an end-to-side anastomosis in a staple-closed configuration.

As shown in FIG. 14, collars 440 and eversion bodies 450 of eversion platforms 410, 420 define inner radius 540 and outer radius 550, respectively, of staple 400. FIG. 15 shows multiple closed staples 400 disposed in a radial plane, with eversion bodies 450 disposed in the anastomotic plane, in an end-to-side anastomosis.

According to embodiments of the invention, a plurality of everting staples can be employed to create a single anastomosis, as shown in FIG. 15, by themselves or optionally in combination with supplemental adhesives, suture, etc. to reduce the number of staples needed. Of course, each eversion platform and staple can be appropriately dimensioned to suit a particular patient, surgical procedure, surgical environment or other factor. Device pairs or combinations of different types or sizes can be used in the same anastomosis, if desired.

As referenced earlier, staple devices according to the multiple embodiments of the invention can be free-standing staples and/or can be connected to a delivery system for the staple device. For example, a flexible element such as suture, suture wire, wire or equivalent (not shown) can extend from a separation point at or near the penetrating element and terminate at a needle (not shown). Staple devices according to embodiments of the invention preferably are made of a biocompatible material, e.g. titanium, stainless steel, nitinol, etc. Such staple devices preferably are malleable, for crimping into a closed position with a closing or crimping device, and/or are constructed of a memory material or other material that can be induced to deform into a desired configuration, e.g. a closed configuration. In the case of a memory material such as nitinol, the staple device can be formed in the closed position, sprung open and delivered to the tissues, and then released from an e.g. delivery system after springing back into a closed position. Such memory material eliminates the need for complicated crimping tools, which are complex and potentially damaging to delicate tissues during deployment due to their bulk and the ergonomics required to deploy them.

Spacing elements according to embodiments of the invention substantially prevent the apposing everting platforms from crushing the cut ends of the vascular or other structures in the anastomosis, by keeping the everting platforms slightly separated from one another in the closed position of the staple. Thus, any tissue in the anastomosis is approximated without being strangulated, consistent with the surgical adage: "approximate, don't strangulate." If the eversion platforms were not kept slightly apart in the closed position, the tissue engaged between them could be crushed to death (necrose) closer to the lumen. With particular reference to e.g. FIGS. 5–7, but also with reference to other embodiments, tissue is engaged in the closed staple with more tissue compression at the spacing elements and less tissue compression at the offset everting platforms. Tissue engagement and compression in this manner accomplishes approximation without strangulation, ensuring viability of the tissue at the most critical point of the anastomosis, namely, the juncture of the two structures being anastomosed.

As referenced above, a plurality of the everting staple devices described herein can be used in a single anastomosis, or a single device can be used. In the case of a single device, one or more sutures, one or more conventional or other type of staples, one or more areas of biological adhesive and/or other means additionally can be used, e.g. at least directly opposite one or each staple device described herein, to complete the anastomosis. In the case of multiple staple devices, whatever the type, it is desirable to space each device at selected points around the circumference of the anastomosis, e.g. at quadrant points (e.g. 12 o'clock, 3 o'clock, 6 o'clock and 9 o'clock positions) or half points (e.g. 12 o'clock and 6 o'clock positions).

Non-everting staple devices can be used at e.g. the heel and toe of an anastomosis formed using a longitudinal (i.e. in the direction of blood flow) opening in the artery or other recipient vessel, and everting staple devices can be used along the sides of the anastomosis between the heel and toe. Such use of non-everting staple devices would reduce the possibility of compromising the circumference of the recipient vessel at the heel and toe. Use of adhesive, suture, or other connection devices or methods in addition to or instead of everting staples can also reduce possible complications and/or the number of everting staple devices needed to form an anastomosis. Staple devices all of the everting type can be used more readily with a transverse (i.e. in the direction perpendicular to blood flow) opening in the recipient vessel.

Of course, each staple can be appropriately dimensioned to suit a particular patient, surgical procedure, surgical environment or other factor. Devices of different sizes can be used in the same anastomosis, if desired.

In use, according to one embodiment, the surgeon or other medical professional penetrates the walls of the vascular or other anatomical structures using one or more needles attached to e.g. suture or other material. The suture, in turn, is attached at or near e.g. a penetrating element of the staple device or to another suitable point at, on, or in association with the staple device. According to alternative embodiments, the staple is a free-standing staple and/or includes delivery mechanisms other than suture and one or more needles.

While the invention has been described with respect to specific embodiments, the invention should not be considered limited to the specific embodiments illustrated and described herein. For example, embodiments of the invention apply not only to anastomoses of vascular structures in e.g. minimally invasive thoracic surgical situations, but also to conventional surgical techniques and to anatomical structures other than vascular structures. Embodiments of the invention apply to anastomosing prosthetic tubular grafts to vascular structures or to each other. Specific features described with respect to one embodiment are also to be considered useable with the other embodiments disclosed and contemplated herein. Other modifications and changes are readily discernible from the specification and will be apparent to those of ordinary skill.

What is claimed is:

1. A surgical staple for use in creating an evened anastomosis of at least two anatomical structures, the staple comprising a staple body constructed for bending and at least two everting elements connected to the staple body, the everting elements protruding from the staple body, the staple body and the everting elements being constructed and arranged so that when the staple body is bent around cut ends of the anatomical structures, the everting elements contact the anatomical structures at everting-element contact locations, the everting elements are in an apposed relationship, and the inner layers of the anatomical structures are held together between the everting elements to form the everted anastomosis; the staple further comprising at least two spacing elements connected to the staple body, the spacing elements being constructed and arranged so that when the staple body is bent around the cut ends of the anatomical structures, the spacing elements contact the anatomical structures at spacing-element contact locations, the spacing elements are in an apposed relationship, and the cut ends of the anatomical structures are held together between the spacing elements; wherein the spacing-element contact locations are closer to each other than the everting-element contact locations are to each other when the staple body is bent, such that the apposed everting elements are generally prevented from crushing the anatomical structures wherein the apposing spacing elements are closer than the apposing everting elements to a bend in the staple body about which the staple is bent around the cut ends of the anatomical structures and the everting elements are disposed closer to a lumen of the anastomosis than the spacing elements are to the lumen.

2. The staple of claim 1, wherein the apposed spacing elements define an inner radius of the bent staple and the apposed everting elements define an outer radius of the bent staple, the radii being taken from the bend in the staple, the inner radius being smaller than the outer radius.

3. The staple of claim 1, wherein one of the spacing elements is disposed along the staple body and the other of the spacing elements is disposed adjacent the staple body.

4. The staple of claim 1, wherein the spacing elements are disposed closer to the middle of the staple than the everting elements.

5. The staple of claim 1, wherein the everting elements are disposed at the very ends of the staple body.

6. The staple of claim 1, further comprising a penetrating element constructed to penetrate all of the at least two anatomical structures when the everting elements are in the apposed relationship.

7. The staple of claim 6, wherein the penetrating element is disposed at only one end of the staple body.

8. The staple of claim 1, wherein one of the everting elements forms a general T-shape with respect to the staple body at one end of the staple; further wherein one other of the everting elements forms a general L-shape with respect to the staple body at another end of the staple.

9. The staple of claim 1, wherein the end of one of the everting elements is aligned with the staple body; further wherein one other of the everting elements is centered on the staple body; such that the staple is asymmetric.

10. The staple of claim 8, wherein one of the everting elements moves laterally with respect to the staple body as the staple is bent, such that the direction of closure of the staple is at an angle to the staple body.

11. The staple of claim 1, wherein the staple body is outside a lumen of the anastomosed anatomical structures when the everting elements are apposed.

12. The staple of claim 1, constructed such that a lumen of the anastomosed anatomical structures is free of exposure to the staple and to cut tissue edges of the anatomical structures.

13. The staple of claim 1, wherein the staple is formed of a memory metal.

14. A surgical staple for use in creation of an everted anastomosis between at least two anatomical structures, the staple comprising means for bending and means for everting connected to and protruding from the means for bending, the means for bending and the means for everting being constructed and arranged so that when the means for bending is bent around cut ends of the anatomical structures, the means for everting forms an apposed relationship and the inner layers of the anatomical structures are held together between the means for everting to form the everted anastomosis; the staple further comprising means for spacing connected to the staple body, the means for spacing being constructed and arranged so that when the staple body is bent about a bend thereof and around the cut ends of the anatomical structures, the means for spacing are in an apposed relationship, the cut ends of the anatomical structures are held together between the means for spacing, the means for spacing are disposed closer to the bend than the means for everting are to the bend, and the means for everting are disposed closer to a lumen of the anastomosis than the means for spacing are to the lumen.

15. The staple of claim 14, wherein the means for everting are disposed on opposite ends of the staple, the means for spacing are disposed on opposite ends of the staple, and the staple further comprises means for penetrating that extends from one of the anatomical structures into one other of the anatomical structures.

16. A surgical staple constructed to join at least two anatomical structures, the staple comprising:
a first everting platform disposed at a first end of the staple, the first everting platform being centered at the first end of the staple;
a second evening platform disposed at a second end of the staple, the second evening platform being connected at one end thereof to the second end of the staple, the first and second evening platforms being constructed to form an evened anastomosis of the anatomical structures;
a first spacing element disposed at the first end of the staple, the first spacing element being disposed adjacent the longitudinal axis of the staple;
a second spacing element disposed at the second end of the staple, the second spacing element being disposed along the longitudinal axis of the staple; and
a single penetrating element for penetrating the anatomical structures, the penetrating element being disposed at the first end of the staple along the longitudinal axis of the staple.

17. The staple of claim 16, wherein the staple is constructed to bend to a closed configuration in which the second evening platform is disposed parallel to the first evening platform and in which the first and second evening platforms are disposed on the same side of the penetrating element.

18. The staple of claim 17, wherein in the closed configuration the first and second spacing elements are apposed.

19. The staple of claim 18, wherein in the closed configuration the first and second spacing elements and the penetrating element define an inner radius of the staple; further wherein in the closed configuration the first and second everting platforms define an outer radius of the staple.

20. The staple of claim 17, wherein in the closed configuration the staple is bent into a "U" shape to form two legs and a bend, the legs of the staple being offset from each other in two dimensions.

21. A device for use in creating an anastomosis of two anatomical structures, the device being constructed to bend to a closed position to create the anastomosis, the anastomosis defining a central lumen, the device comprising:
penetration structure for penetrating and holding both anatomical structures at the anastomosis; and
eversion structure for everting an end of at least one of the anatomical structures, the eversion structure being disposed closer to the lumen of the anastomosis than the penetration structure and the penetration structure being disposed closer to the bend than any portion of the eversion structure is disposed to the bend when the device is in the closed position, the eversion structure being constructed to accommodate the anatomical structures wherein the eversion structure forms a general T-shape at one end of the device and forms a general L-shape at another end of the device.

22. The device of claim 21, wherein the device is constructed from a memory metal such that a crimping tool is unnecessary to create the anastomosis.

23. The device of claim 21, further comprising spacing structure for providing space within the eversion structure to minimize tissue necrosis in the anatomical structures.

24. The device of claim 21, wherein the device is a surgical staple, further wherein the penetration structure defines an inner radius of the staple and the eversion structure defines an outer radius of the staple, placement of the inner radius and outer radius causing the staple to be excluded from the lumen of the anastomosis.

25. The device of claim 21, wherein the device is a surgical staple having a staple body, further wherein the eversion structure comprises two everting platforms protruding from the staple body.

26. The device of claim 21, wherein the device is an everting surgical staple, the everting surgical staple being in combination with at least one non-everting surgical staple to form the anastomosis.

27. A surgical staple for use in creating an everted anastomosis of at least two anatomical structures, the staple comprising a generally cylindrical staple body constructed for bending and at least two everting elements connected to opposite ends of the staple body, the everting elements being of generally the same length and protruding from the staple body, one of the everting elements being constructed to protrude from the staple body more than another of the everting elements protrudes from the staple body, the staple body and the everting elements being constructed and arranged so that when the staple body is bent around cut ends of the anatomical structures, the everting elements are in an apposed relationship and the inner layers of the anatomical structures are held together between the everting elements to form the everted anastomosis wherein at least two spacing elements are connected to the staple body, the spacing elements being constructed and arranged so that when the staple body is bent around the cut ends of the anatomical structures, the spacing elements are in apposed relationship and the cut ends of the anatomical structures are held together between the spacing elements, and a penetrator for penetrating that extends from one of the anatomical structures into another of the anatomical structures.

28. The staple of claim 27, wherein the evening elements are offset from each other transversely with respect to the staple body; further wherein one of the everting elements is off-center on the staple body; further wherein one other of the everting elements is centered on the staple body.

29. The staple of claim 27, wherein the staple body twists and one of the everting elements moves laterally with respect to the staple body as the staple is bent, such that the direction of closure of the staple is at an angle to the staple body.

30. The staple of claim 27, wherein each of the everting elements defines first and second ends, the staple body and everting elements being constructed and arranged so that when the staple body is bent around cut ends of the anatomical structures, the lengths of the everting elements are aligned such that the first ends are aligned with each other and the second ends are aligned with each other.

\* \* \* \* \*